(12) United States Patent
Shirasaki et al.

(10) Patent No.: US 7,236,889 B2
(45) Date of Patent: Jun. 26, 2007

(54) METHOD OF EXAMINING FOREIGN MATTER DERIVED FROM LIVING BODY

(75) Inventors: Yoshinari Shirasaki, Tsukuba (JP); Naoyuki Nishimura, Tsukuba (JP)

(73) Assignee: Shimadzu Corporation (JP)

( * ) Notice: Subject to any disclaimer, the term of this patent is extended or adjusted under 35 U.S.C. 154(b) by 381 days.

(21) Appl. No.: 10/370,759

(22) Filed: Feb. 24, 2003

(65) Prior Publication Data

US 2003/0170709 A1    Sep. 11, 2003

(30) Foreign Application Priority Data

Mar. 6, 2002   (JP) .............................. 2002-060923

(51) Int. Cl.
*G06F 19/00* (2006.01)
*C12Q 1/68* (2006.01)
*C12N 15/10* (2006.01)

(52) U.S. Cl. ............................. 702/19; 435/6; 536/24.3

(58) Field of Classification Search ..................... None
See application file for complete search history.

(56) References Cited

FOREIGN PATENT DOCUMENTS

| JP | 03-009483 | 1/1991 |
|---|---|---|
| JP | 10-151125 | 6/1998 |
| JP | 11-183118 | 7/1999 |
| JP | 2001-340072 | 12/2001 |

OTHER PUBLICATIONS

Bidawid et al. Contamination of Foods by Food Handlers: Experiments on Hepatitis A Virus Transfer to Food and Its Interruption Applied and Environmental Microbiology vol. 66, pp. 2759-2763 (2000).*
Chin En Yan, Hua Zhong Technology University, "Court Medical DNA Type", Chinese Court Medical Journal, Year 2001, vol. 16, No. 1, pp. 58-60.
Chinese Patent Office 1st Office Action issued on Jul. 2, 2004.

\* cited by examiner

*Primary Examiner*—John S. Brusca
(74) *Attorney, Agent, or Firm*—Rader Fishman and Grauer PLLC

(57) ABSTRACT

The present invention provides a method for examining a foreign matter derived from a living body in quality control for production of various products in order to rapidly identify an individual from whom a living body-derived material contaminated as a foreign matter in products or facilities involved in production of the products was derived, while securing the secret of information on nucleic acid sequences unique to individuals. The method for examining a foreign matter derived from a living body includes identifying an individual from whom a living body-derived material contaminated as a foreign matter in products or facilities involved in production of the products was derived, on the basis of information on sequences of nucleic acid contained in the living body-derived material.

18 Claims, 2 Drawing Sheets

Fig. 2  OUTLINE OF EXAMINATION OF ORIGIN OF HAIR CONTAMINATED IN A PROCESS OF MANUFACTURING FOODS
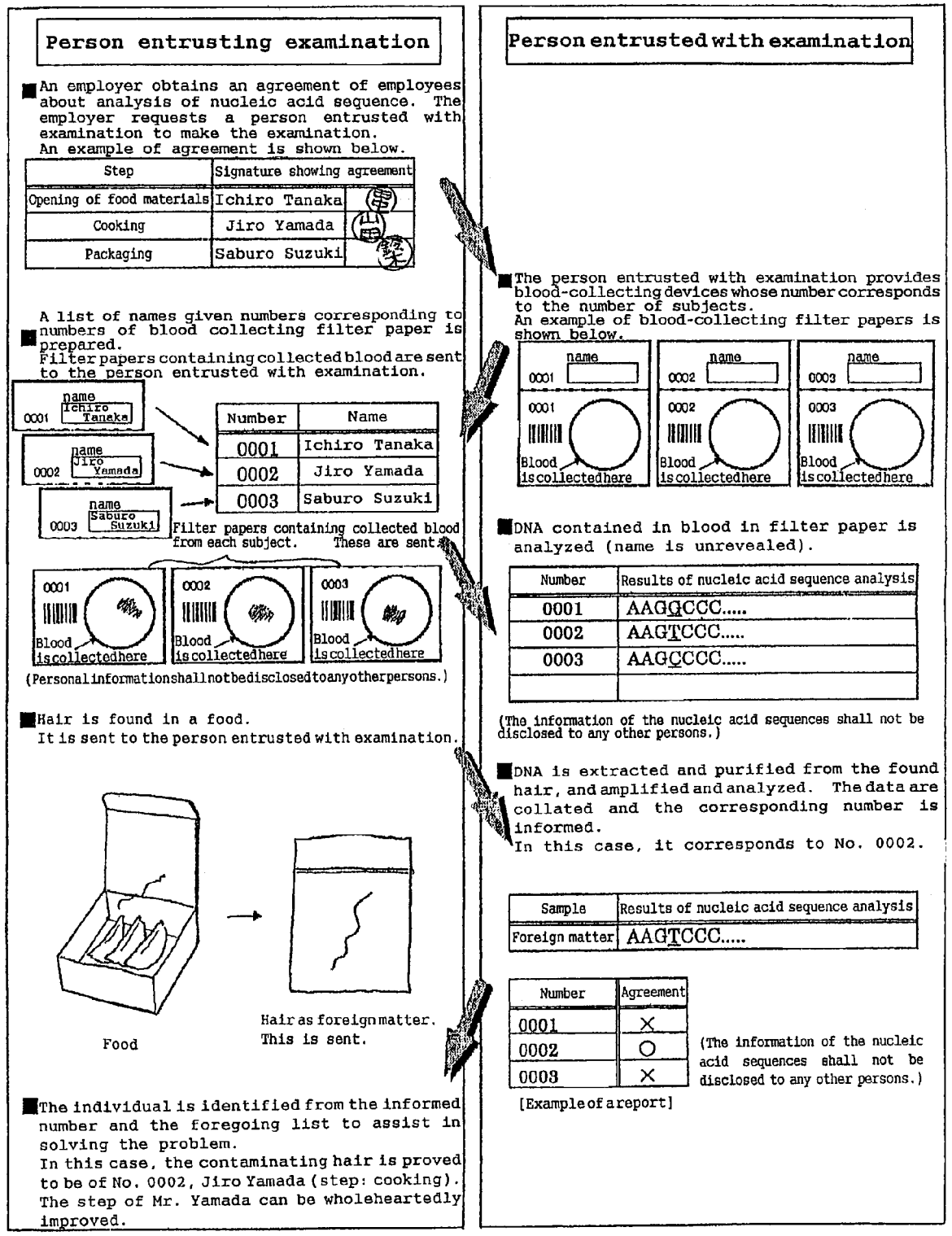

METHOD OF EXAMINING FOREIGN MATTER DERIVED FROM LIVING BODY

BACKGROUND OF THE INVENTION

1. Field of the Invention

The present invention relates to a technique of quality control for production of various products, and to a method for examining a foreign matter derived from a living body in order to identify an individual from whom a living body-derived material contaminated as a foreign matter in products or facilities involved in production of the products was derived. Particularly, the present invention relates to a technique of quality control for production of foods or the like whose qualities are significantly influenced by contamination of such products with a living body-derived material such as hair as a foreign matter.

2. Disclosure of the Related Art

It is generally known that upon contamination of foods or the like with a living body-derived foreign matter such as hair, the qualities of such products are significantly deteriorated. However, identification of the origin of the contaminating foreign mater has been regarded as difficult and not generally performed.

On the other hand, identification of individuals on the basis of DNA sequences contained in living body-derived materials such as hair is actively performed in recent years in the fields of forensic medicine and forensic science, and identification by DNA for the purpose of parentage test or the like is performed by private enterprises.

However, application of information on DNA sequences to quality control in production of various products has never been performed.

SUMMARY OF THE INVENTION

Rapid identification of the origin (usually an individual) of a living-body derived foreign matter, particularly hair or the like, contained in products or in facilities, units, instruments, fixtures, parts or the like where products may be contaminated with a foreign matter is an important task in improving a process of manufacturing products such as foods whose values are significantly deteriorated by contamination with a foreign matter. If rapid identification is feasible, the individual causing contamination with a foreign matter is asked about circumstances for investigation of the reason for contamination with the foreign matter, and the individual in question is advised and effective measures can be taken to improve the production process.

However, the investigation of a contaminating foreign matter (collection of evidence or the like) is usually performed after the foreign matter is found, and in this case, the evidence is scattered and lost with time to take time for collection of information and is poor in reliability. Under the circumstances, it is therefore difficult to identify its cause based on investigation results and to take effective measures on the basis of the identified cause. The present invention solves these problems and contributes to improvements in the qualities of products, particularly foods.

Further, information on nucleic acid sequences such as DNA is information unique to individuals, and the secret of the information on nucleic acid sequences should be secured.

An object of the present invention is to provide a method for examining a foreign matter derived from a living body in quality control for production of various products, in order to identify an individual from whom a living body-derived material contaminated as a foreign matter in products or facilities involved in production of the products was derived. In particular, an object of the present invention is to provide a method for examining a foreign matter derived from a living body in quality control for production of foods or the like whose qualities are influenced significantly by contamination of products with a living body-derived material such as hair as a foreign matter, in order to identify an individual from whom a living body-derived material contaminated as a foreign matter in products or facilities involved in production of the products was derived.

Another object of the present invention is to provide a method for examining a foreign matter derived from a living body in order to rapidly identify an individual from whom a living body-derived material contaminated as a foreign matter in products or facilities involved in production of the products was derived, while securing the secret of information on nucleic acid sequences unique to individuals.

The present invention encompasses following inventions:

(1) A method for examining a foreign matter derived from a living body, which comprises identifying an individual from whom a living body-derived material contaminated as the foreign matter in products or facilities involved in production of the products was derived, on the basis of information on sequences of nucleic acid contained in the living body-derived material. The individual is usually an individual having an opportunity to contaminate the products or the facilities involved in production of the products with a living body-derived material. The facilities involved in production of the products comprehensively encompass facilities, units, instruments, fixtures, parts or the like used in production steps including packaging and shipment.

(2) The method for examining a foreign matter derived from a living body according to the above-mentioned (1), wherein the nucleic acid is DNA.

(3) The method for examining a foreign matter derived from a living body according to the above-mentioned (1), wherein the nucleic acid is RNA.

(4) The method for examining a foreign matter derived from a living body according to any of the above-mentioned (1) to (3), wherein the products are foods. When products such as foods are contaminated with a living material such as hair, product qualities are significantly deteriorated, so application of the present invention to foods is of great value.

(5) The method for examining a foreign matter derived from a living body according to any of the above-mentioned (1) to (4), wherein the living body-derived material is hair. Foods are easily contaminated with hair as a living body-derived material.

(6) The method for examining a foreign matter derived from a living body according to any of the above-mentioned (1) to (5), wherein a nucleic acid-containing materials such as blood, hair, skin, nail or oral mucous membrane from individuals having an opportunity to contaminate the products or the facilities involved in production of the products with the living body-derived material is collected before production of products, and a nucleic acid sequences contained in the nucleic acid-containing materials are previously analyzed. The nucleic acid-containing materials include, but are not limited to, blood, hair, skin, nail and oral mucous membrane. By doing so, when a living body-derived material is actually contaminated as a foreign matter, the nucleic acid sequence of the contaminating living body-derived material can be analyzed for rapid identification.

(7) The method for examining a foreign matter derived from a living body according to the above-mentioned (6), wherein the nucleic acid sequence of the living body-derived material contaminated as the foreign matter is collated with the previously analyzed nucleic acid sequences thereby identifying the individual from whom the contaminating living body-derived material was derived. By doing so, rapid examination and identification is made feasible upon actual contamination with a living body-derived material as a foreign matter.

(8) The method for examining a foreign matter derived from a living body according to the above-mentioned (6), wherein a person entrusting examination, usually a manufacturer of the products, collects the nucleic acid-containing materials from all the individuals having an opportunity to contaminate the products or the facilities involved in production of the products with the living body-derived material, thus obtaining samples before production of the products, then gives the collected samples numbers or symbols not connected to personal informations such as name, and provides the collected samples together with the given numbers or the given symbols without disclosure of the personal informations, to a person entrusted with examination, to request him to analyze the nucleic acid sequences, and the person entrusted with examination analyzes the nucleic acid sequences in the samples requested to be examined, and then stores the analyzed informations of the nucleic acid sequences as analysis data of nucleic acid sequences with correspondence to the given numbers or the given symbols without disclosure to the person entrusting examination. The person who entrusts examination is usually a manufacturer of the products. The person entrusted with examination is usually an institution or a company which can analyze the nucleic acid sequences. By so doing, rapid identification while securing the secret of information on the nucleic acid sequences unique to individuals is made feasible upon actual contamination with a living body-derived material as a foreign matter by analyzing the nucleic acid sequence of the contaminating living body-derived material.

(9) The method for examining a foreign matter derived from a living body according to the above-mentioned (8), wherein upon actual contamination of the products or the facilities involved in production of the products with the living body-derived material as the foreign matter, the person entrusting examination provides the contaminating living body-derived material to the person entrusted with examination, to request him to analyze its nucleic acid sequence, and the person entrusted with examination analyzes the nucleic acid sequence of the contaminating living body-derived material and collates the nucleic acid sequence with the analysis data of nucleic acid sequences thereby determining which number or symbol to which the nucleic acid sequence of the contaminating living body-derived material corresponds or determining whether there is a nucleic acid sequence in the data corresponding to the nucleic acid sequence of the contaminating living body-derived material, and informs the person entrusting examination of the corresponding number or the corresponding symbol, or of no correspondence to any of the numbers or the symbols. By so doing, rapid examination and identification while securing the secret of information on the nucleic acid sequences unique to individuals is made feasible upon actual contamination with a living body-derived material as a foreign matter.

(10) The method for examining a foreign matter derived from a living body according to the above-mentioned (9), wherein the person entrusting examination idenifies the individual from whom the living body-derived material was derived, on the basis of the informed number or the informed symbol.

(11) The method for examining a foreign matter derived from a living body according to any of the above-mentioned (1) to (10), wherein the nucleic acid sequence to be examined is a nucleic acid derived from mitochondria.

(12) The method for examining a foreign matter derived from a living body according to any of the above-mentioned (1) to (11), wherein the examination of the nucleic acid is carried out by a sequencing method.

(13) The method for examining a foreign matter derived from a living body according to any of the above-mentioned (1) to (11), wherein the examination of the nucleic acid sequence is performed by a method for detecting base substitution, insertion or deletion, or a method for counting the number of minisatellite or microsatellite. Above mentioned methods in (12) and (13) maybe used in combination, depending on the purposes.

(14) The method for examining a foreign matter derived from a living body according to any of the above-mentioned (1) to (13), wherein nucleic acid amplification is performed before examination of the nucleic acid sequence.

(15) The method for examining a foreign matter derived from a living body according to any of the above-mentioned (1) to (14), wherein elementary analysis such as X-ray fluorescence spectrometry, ICP atomic emission spectrometry, ICP mass spectrometry, atomic absorption spectrometry or PIXE is simultaneously used to increase a probability of identification of the individual.

(16) The method for examining a foreign matter derived from a living body according to any of the above-mentioned (1) to (14), wherein infrared, visible or ultraviolet absorption spectrophotometry is simultaneously used to increase a probability of identification of the individual.

(17) The method for examining a foreign matter derived from a living body according to any of the above-mentioned (1) to (14), wherein a method for observing a fine surface shape under an optical microscope, a laser microscope, an atomic force microscope or a scanning electron microscope is simultaneously used to increase a probability of identification of the individual.

By the method of the present invention, in the case where a foreign matter derived from a living body is found in products or facilities, its origin can be specified rapidly and certainly after finding. Specific information on this origin can be reliable evidence showing what is responsible for the foreign matter. By revealing what is responsible for the foreign matter, the process can be improved to reduce defectives containing the foreign matter, or a worker in charge of the production can be suitably dealt with by sharing responsibility for compensation or by reward and punishment or the like. On one hand, workers not responsible for contamination with the foreign matter can be provided with reliable evidence showing that they are not responsible for the contamination.

The present invention functions usefully in stably providing products of higher qualities. As illustrated in the Example, when hair is contained in a certain food, the step in which the contamination caused is not clear in the prior art, to make it difficult to solve the problem by improving the step. According to the present invention, however, the step in which the contamination caused can be revealed rapidly and certainly, and thus rapid improvement of the step is feasible, and thereafter the probability of contamination of products with hair can be significantly reduced. Accordingly, it can be said that foods produced by carrying out the method for examining a living body-derived foreign matter according to the present invention are more sanitary than foods produced without carrying out the method of the present invention. Further, even if a certain foreign matter derived from a living body is found and complained of by a consumer, the complaint can be dealt with more rapidly and certainly, which leads to providing more sanitary foods.

BRIEF DESCRIPTION OF THE DRAWINGS

FIG. 2 is a flow chart showing a more specific embodiment of the method for examining a living-body derived foreign matter according to the present invention, wherein the origin of hair contaminated in a process for producing foods is examined.

DETAILED DESCRIPTION OF THE INVENTION

Figure 1:
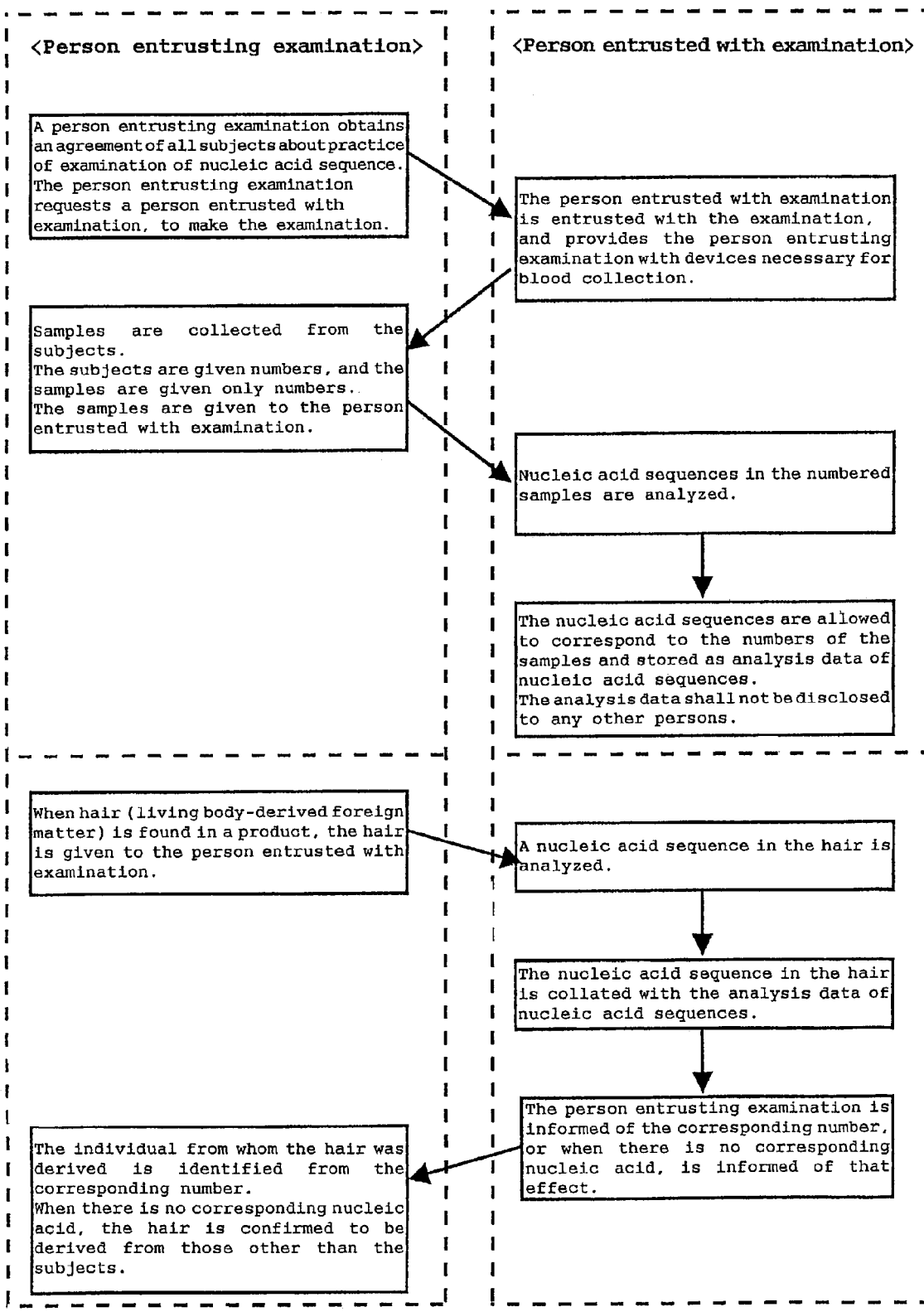
FIG. 1 is a flow chart showing an embodiment of a method for examining a living-body derived foreign matter according to the present invention.

Hereinafter, a method for examining a living-body derived foreign matter according to the present invention will be described with reference to FIGS. 1 and 2.

First, those entrusting examination such as a manufacturer obtains an agreement with all individuals (usually employees) who may contaminate products or facilities involved in production of the products with foreign matters about practice of analysis of their nucleic acid sequences, and then requests those entrusted with examination, such as an institution or company analyzing nucleic acid sequences, to make the examination.

Those entrusted with examination provide those entrusting examination with materials necessary for collection of samples. FIG. 2 shows blood-collecting paper filters as the materials for collection of samples.

Those entrusting examination collect samples from all individuals of subjects before they work in manufacturing. The usable samples include, but are not limited to, biological materials such as blood, hair, skin and oral mucous membrane. FIG. 2 shows that as the sample, blood is collected in a blood-collecting filter paper. In this occasion, those entrusting examination have previously given the numbers (or symbols) not connected to personal information (names and the like) to the collected samples and prepared a list of correspondence between the numbers (or the symbols) and the names. Those entrusting examination shall not disclose this list and personal information to other persons including those entrusted with examination.

Those entrusting examination provide those entrusted with examination, with the collected samples given the numbers (or the symbols) only, and request them to analyze nucleic acid sequences of the respective samples. In this occasion, those entrusting examination shall give only the samples given the numbers (or the symbols) to those entrusted with examination, and shall not disclose information enabling identification of the individuals.

Those entrusted with examination perform analysis of a nucleic acid sequence of each sample (decoding of nucleic acid sequence or classification of its type). Then, the determined nucleic acid sequence of each sample is allowed to correspond to the number (or symbol) assigned to the sample, and stored as analysis data of nucleic acid sequences. An example of the analysis data of nucleic acid sequences is shown in FIG. 2. Those entrusted with examination shall not disclose the analysis data of nucleic acid sequences to other persons including those entrusting examination. By so doing, the nucleic acid sequence data unique to the individuals can be prevented from leaking out.

In this manner, the secret of information on the nucleic acid sequences unique to the individuals can be secured to be in state where rapid dealing with the case of actual contamination of products or facilities involved in production of the products with a living body-derived material as a foreign matter is feasible.

Now, the case where products or facilities involved in production of the products are contaminated with a living body-derived material as a foreign matter will be described.

Those entrusting examination, that is, a manufacturer of the products, find a living body-derived material contaminated as a foreign matter in the products or the facilities involved in production of the products, or a person other than the manufacturer, such as distributors or consumers, find a living body-derived material contaminated as a foreign matter in the products, and provide the living body-derived material to the manufacturer. An example of contamination of a food with human hair is shown in FIG. 2. Those entrusting examination provide the found or provided living body-derived material to those entrusted with examination, and request them to analyze the nucleic acid sequence of the living body-derived material.

Those entrusted with examination analyze the nucleic acid sequence of the living body-derived material (decoding of nucleic acid sequence or classification of its type), then collate the analyzed nucleic acid sequence with the previously prepared and stored analysis data of nucleic acid sequences, and inform those entrusting examination of its corresponding number (or symbol). When there is no corresponding nucleic acid in the analysis data of nucleic acid sequences, those entrusted with examination inform those entrusting examination of that effect.

On the basis of the examination results informed by those entrusted with examination, those entrusting examination identify the individual from whom the found living body-derived material was derived. If the person causing contamination with the foreign matter can be rapidly identified, those entrusting examination ask the individual causing contamination with the foreign matter about circumstances to investigate the cause of contamination with the foreign matter, and advise the individual to take notice or take effective measures to be able to improve the production process rapidly.

On the other hand, when there is no corresponding nucleic acid sequence, it is possible to take measures targeting at received materials, contamination after manufacturing or intentional contamination with the foreign matter.

For examination of the nucleic acid sequence, it is possible to use various sequencing methods (nucleotide sequencing), a method for detecting base substitution such as a method for analyzing various single nucleotide polymorphisms (SNPs) [Cargill, M. et al.: Nature Genetics 22, 231–238 (1999): Characterization of single-nucleotide polymorphisms in coding regions of human genes], a method for detecting insertion or deletion, a method for counting the number of repeated sequences (minisatellite, macrosatellite) (variable number of tandem repeats (VNTR) and short tandem repeats (STR)) [Nakamura, Y. et al.: Science 235, 1616–1622 (1987): Variable number of tandem repeat (VNTR) markers for human gene mapping], etc.

The sequencing method includes, but is not limited to, the Sanger method, the Maxam-Gilbert method, a Pyrosequence method [Ronaghi, M. et al.: Science 281, 363–365 (1998); A sequencing method based on real-time pyrophosphate] etc.

The method for analyzing SNPs includes, but is not limited to, a hybridization method using DNA microarrays [Patrick, O. B. et al.: Nature Genetics 21, 33–37 (1999): Exploring the new world of the genome with DNA microarrays] etc., an invader method [Victor, L. et al.: Nature Biotechnology 17, 292–296 (1999): Polymorphism identification and quantitative detection of genomic DNA by invasive cleavage of oligonucleotide probes], a Taqman probe method [Shi, M.M.: Clin Chem 47, 164–172 (2001): Enabling large-scale pharmacogenetic studies by high-throughput mutation detection and genotyping technologies], a Masscode tag method [High-throughput SNP genotyping using Masscode™ technology, Qiagen News. Issue No. 2, 2001], an allele specific PCR method [Soren, G. et al.: Genome Res 10, 258–266 (2000): High-throughput SNP allele-frequency determination in pooled DNA samples by kinetic PCR], an RFLP method [Jazwinska, E. C. et al.: Am J Hum Genet 43, 175–181 (1988): Gm typing by immunoglobulin heavy-chain gene RFLP analysis] etc.

A general method for counting the number of repeated sequences includes, but is not limited to, a method wherein a DNA region containing repeated sequences is amplified and then the molecular weight of the amplified DNA is examined by electrophoresis.

Above-mentioned methods for examining nucleic acids may be used in combination, depending on purposes.

Prior to examination of nucleic acid sequence, nucleic acid amplification is generally performed. Known methods of amplifying nucleic acid include, but are not limited to, a PCR method [Saiki, R. K. et al.: Science 230, 1350–1354 (1985): Enzymatic amplification of beta-globin genomic sequences and restriction site analysis for diagnosis of sickle cell anemia], an LAMP method [Notomi, T. et al.: Nucleic Acids Res, 28(12), e63 (2000): Loop-mediated isothermal amplification of DNA], an ICAN method [innovative method for DNA amplification at a constant temperature, ICAN method, TAKARA BIO INC. News Release, Sep. 25, 2000] and a TMA method [Jonas, V. et al.: J Clin Microbiol 31, 2410–2416 (1993): Detection and identification of Mycobacterium tuberculosis directly from sputum sediments by amplification of rRNA]. For amplification of nucleic acid, an Ampdirect reagent for inhibiting the influence of various inhibitors of nucleic acid amplification [Nishimura, N. et al.: Ann Gun Biochem 37, 674–680 (2000): Direct PCR from whole blood without DNA isolation] can be used.

As the sites of nucleic acid to be examined, sites mutated among individuals are selected. Such sites exist in mitochondria DNA or nucleic DNA. In mitochondria DNA, the D-LOOP region is known as a highly mutated region. Further, in nucleic DNA, the number of minisatellite•microsatellite repeats (VNTR•STR) is known to vary among individuals, and used often in identification of individuals in forensic medicine or the like. Further, identification of individuals can be performed by analyzing a necessary number of SNPs. However, the sites of nucleic acid to be examined is not limited to those sites, but maybe selected from the sites of base substitution, insertion, and deletion. The sites mentioned above may be selected in combination, depending on the purposes.

When a living body-derived foreign matter is found in a products or facilities involves in production of the products, a nucleic acid sequence contained therein is immediately analyzed and collated with the preciously prepared and stored analysis data of nucleic acid sequences, to identify an individual as the source of the foreign matter. In the present invention, a variety of supplementary analysis and observation methods such as elementary analysis methods (X-ray fluorescence spectrometry, ICP atomic emission spectrometry, ICP mass spectrometry, atomic absorption spectrometry or PIXE), light (infrared, visible, ultraviolet) absorption spectrophotometry, a method for observing a fine surface shape under an optical microscope, a laser microscope, an atomic force microscope or a scanning electron microscope can be used in combination to obtain supporting evidence for identifying the individual thereby raising the probability of identification. For example, in the case of hair, the characteristics such as a degree of dyeing or decoloring, thickness and roughness of the hair can be obtained to provide supporting evidence for identifying the individual in examination of the foreign matter.

As described above, according to the method for examining a living body-derived foreign matter in the present invention, it is possible to rapidly identify an individual from whom a living body-derived material contaminated as a foreign matter in products or facilities involved in production of the products was derived, while securing the secret of information on nucleic acid sequences unique to individuals.

That is, the previous analysis of nucleic acid sequences unique to individuals having an opportunity to contaminate products or facilities involved in production of the products with a living body-derived material before they work in manufacturing brings about a significant reduction in the time for examination of a living body-derived foreign matter, as well as improvements in reliability of the examination. This is because targeting at subjects necessary for the examination, the procedure of obtaining an agreement about the examination, and the analysis of nucleic acid sequences of the subjects are carried out before occurrence of contamination with a foreign matter so that upon actual finding of a foreign matter, the analysis of the nucleic acid sequence of the foreign matter and the procedure of identification can be immediately performed.

On one hand, the nucleic acid sequence is important personal information, and should be handled particularly cautiously. In this respect, the method of the present invention can prevent personal nucleic acid sequence information from leaking out because those entrusting examination have no means to know information on nucleic acid sequence, while those entrusted with examination have no means to know personal information.

Given the conditions described above, the examination of nucleic acid sequences of individuals can be introduced into the control of production process, and upon contamination of products or facilities involved in production of the products with a living body-derived foreign matter, the origin of the living body-derived foreign matter can be examined certainly in a short time.

EXAMPLE

Hereinafter, a further concrete example will be described, but the present invention is not limited to this example and can be carried out in various modes.

1. A manufacturer producing a food A, that is, a person entrusting examination of nucleic acid sequence, is involved in production of the food A and selects individuals having an opportunity to contaminate the food A with a foreign matter (hair or the like) as subjects of examination of nucleic acid sequence.

2. The person entrusting examination obtains an agreement of all the subjects about practice of the examination of nucleic acid sequence.

3. Before production of the food A, the person entrusting examination requests a person entrusted with examination, to make the examination of nucleic acid sequence with respect to production of the food A.

4. The person entrusted with examination supplies the person entrusting examination with blood collection devices, the number of which corresponds to the number of the subjects. A filter paper is used for collection of blood from each individual. Each filter paper is given a different number (serial number) and bar code.

5. By the person entrusting examination, blood from each individual is collected on each of the filter papers. The filter papers each containing collected blood are collected, and a list where the number on the filter paper containing blood corresponds to the individual from whom the blood was collected is prepared and stored as information. This information shall not be disclosed to the person entrusted with examination.

6. The person entrusting examination provides the filter papers containing collected blood to the person entrusted with examination, and requests examination of their nucleic acid sequences. Each filter paper containing collected blood does not have any description of personal information such as name.

7. The person entrusted with examination receives the filter papers containing collected blood from the person entrusting examination, and analyzes their nucleic acid sequences. Depending on the number of the subjects, the sites of the sequence to be examined shall be increased or decreased to give satisfactory probability. The obtained information on the nucleic acid sequence is allowed to correspond to the serial number and stored. Specifically, apart of DNA in blood contained in the filter paper is amplified by techniques such as PCR to obtain the information on its sequence by using a DNA sequencer. For amplification of DNA in blood in the filter paper, an Amp direct reagent for suppressing the inhibition by blood components on amplification can be used. For procedures such as inputting serial numbers into a computer, a bar code reader can be used. The analysis data of nucleic acid sequences thus obtained shall not be disclosed not only to the person entrusting examination but also to any other persons.

8. When a foreign matter (hair) is actually found in the food A, the person entrusting examination sends the hair to the person entrusted with examination.

9. The person entrusted with examination examines a DNA sequence contained in the sent hair, and collates it with the sequences of the subjects contained in the analysis data of nucleic acid sequences. If there is its corresponding sequence, the person entrusting examination is informed of its serial number. When there is no corresponding sequence, the person entrusting examination is informed of that effect.

10. The person entrusting examination identifies the individual on the basis of the serial number obtained from the person entrusted with examination. The person entrusting examination asks the identified individual about circumstances, to investigate the cause of contamination with the foreign matter, and advise the individual to take notice or take effective measures to be able to improve the production process. On the other hand, when there is no corresponding sequence, it is possible to take measures targeting at received materials, contamination after manufacturing or intentional contamination with the foreign matter.

The example described above shows one embodiment of the method for examining a living body-derived foreign matter according to the present invention. However, the present invention can be carried out in various forms. Accordingly, the example described above is described for merely illustrative purposes and not construed as being restrictive. Further, any modifications falling under an equivalent to the claims are within the scope of the present invention.

What is claimed is:

1. A method for examining a foreign matter derived from a living body, which method comprises
    identifying an individual from whom a living body-derived material is derived on the basis of information analyzed on a nucleic acid sequence contained in the living body-derived material,
    wherein said living body-derived material contaminates a product or a facility involved in production of said product, and
    wherein a nucleic acid-containing material from an individual having an opportunity to contaminate said product or facility is collected before production of products, and a nucleic acid sequence contained in the nucleic acid-containing material is analyzed before production of products.

2. The method for examining a foreign matter derived from a living body according to claim 1, wherein said nucleic acid sequence is a DNA sequence.

3. The method for examining a foreign matter derived from a living body according to claim 1, wherein said nucleic acid sequence is a RNA sequence.

4. The method for examining a foreign matter derived from a living body according to claim 1, wherein the product is food.

5. The method for examining a foreign matter derived from a living body according to claim 1, wherein the living body-derived material is hair.

6. The method for examining a foreign matter derived from a living body according to claim 1, wherein said nucleic acid-containing material is selected from the group consisting of blood, hair, skin, nail and oral mucous membrane.

7. The method for examining a foreign matter derived from a living body according to claim 1, wherein the nucleic acid sequence of the living body-derived material that contaminates said product or facility is collated with the nucleic acid sequence contained in the nucleic acid-containing material analyzed before production of products, thereby identifying the individual from whom the contaminating living body-derived material is derived.

8. The method for examining a foreign matter derived from a living body according to claim 1, wherein a manufacturer of said product collects the nucleic acid-containing materials from all the individuals having an opportunity to contaminate said product or facility, thus obtaining samples before production of the products, then gives the collected samples numbers or symbols not connected to personal information such as name, and provides the collected samples together with the given numbers or the given symbols without disclosure of the personal information, to an institution or a company which can analyze a nucleic acid sequence, to request said institution or company to analyze the nucleic acid sequences of the collected samples, and
    said institution or company analyzes the nucleic acid sequences in the samples requested to be examined, and then stores the analyzed information of the nucleic acid sequences as analysis data of nucleic acid sequences with correspondence to the given numbers or the given symbols without disclosure to said manufacturer.

9. The method for examining a foreign matter derived from a living body according to claim 8, wherein upon actual contamination of said product or facility, said manufacturer provides the contaminating living body-derived material to said institution or company, to request said institution or company to analyze the nucleic acid sequence of the contaminating living body-derived material, and said institution or company analyzes the nucleic acid sequence of the contaminating living body-derived material and collates the nucleic acid sequence of the contaminating living body-derived material with the analysis data of nucleic acid sequences thereby determining which number or symbol to which the nucleic acid sequence of the contaminating living body-derived material corresponds or determining whether there is a nucleic acid sequence in the data corresponding to the nucleic acid sequence of the contaminating living body-derived material, and informs said manufacturer of the corresponding number or the corresponding symbol, or of no correspondence to any of the numbers or the symbols.

10. The method for examining a foreign matter derived from a living body according to claim 9, wherein said manufacturer identifies the individual from whom the living body-derived material is derived, on the basis of the informed number or the informed symbol.

11. The method for examining a foreign matter derived from a living body according to claim 1, wherein the nucleic acid sequence to be examined is derived from mitochondria.

12. The method for examining a foreign matter derived from a living body according to claim 1, wherein the analysis of the nucleic acid sequence is carried out by a sequencing method.

13. The method for examining a foreign matter derived from a living body according to claim 1, wherein the analysis of the nucleic acid sequence is performed by a method for detecting base substitution, insertion or deletion, or a method for counting the number of minisatellite or microsatellite.

14. The method for examining a foreign matter derived from a living body according to claim 1, wherein nucleic acid amplification is performed before analysis of the nucleic acid sequence.

15. The method for examining a foreign matter derived from a living body according to claim 1, wherein elementary analysis is simultaneously used to increase a probability of identification of the individual.

16. The method for examining a foreign matter derived from a living body according to claim 15, wherein the elementary analysis is selected from the group consisting of X-ray fluorescence spectrometry, ICP atomic emission spectrometry, ICP mass spectrometry, atomic absorption spectrometry or PIXE.

17. The method for examining a foreign matter derived from a living body according to claim 1, wherein infrared, visible or ultraviolet absorption spectrophotometry is simultaneously used to increase a probability of identification of the individual.

18. The method for examining a foreign matter derived from a living body according to claim 1, wherein a method for observing a fine surface shape under an optical microscope, a laser microscope, an atomic force microscope or a scanning electron microscope is simultaneously used to increase a probability of identification of the individual.

* * * * *